(12) United States Patent
Bleckmann et al.

(10) Patent No.: US 7,138,128 B2
(45) Date of Patent: *Nov. 21, 2006

(54) PREPARATIONS OF THE W/O EMULSION TYPE WITH AN INCREASED WATER CONTENT, AND COMPRISING CATIONIC POLYMERS

(75) Inventors: Andreas Bleckmann, Ahrensburg (DE); Rainer Kröpke, Schenefeld (DE); Günther Schneider, Hamburg (DE)

(73) Assignee: Beiersdorf AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 561 days.

(21) Appl. No.: 09/436,171

(22) Filed: Nov. 9, 1999

(65) Prior Publication Data

US 2002/0146438 A1 Oct. 10, 2002

(30) Foreign Application Priority Data

Nov. 19, 1998 (DE) ................................. 198 53 281
Nov. 30, 1998 (DE) ................................. 198 55 153

(51) Int. Cl.
*A61K 6/00* (2006.01)
*A61K 7/00* (2006.01)

(52) U.S. Cl. ........................ 424/401; 514/937; 514/55; 424/59

(58) Field of Classification Search ................ 424/401, 424/78.02; 516/22; 282/209; 514/55, 937
See application file for complete search history.

(56) References Cited

U.S. PATENT DOCUMENTS

| | | | | |
|---|---|---|---|---|
| 4,976,952 A | * | 12/1990 | Lang et al. | 424/47 |
| 5,015,469 A | * | 5/1991 | Yoneyama et al. | 424/59 |
| 5,053,220 A | * | 10/1991 | Arraudeau et al. | 424/63 |
| 5,478,562 A | * | 12/1995 | Cauwet et al. | 424/401 |
| 5,830,483 A | * | 11/1998 | Seidel et al. | 424/401 |
| 5,935,589 A | * | 8/1999 | Mukherjee et al. | 424/401 |
| 6,013,270 A | * | 1/2000 | Hargraves et al. | 424/401 |
| 6,051,211 A | * | 4/2000 | Hansenne et al. | 424/59 |
| 6,113,890 A | * | 9/2000 | Young et al. | 424/70.11 |
| 6,338,858 B1 | * | 1/2002 | Dupuis et al. | 424/486 |

FOREIGN PATENT DOCUMENTS

| | | |
|---|---|---|
| WO | 98/17232 | 4/1998 |
| WO | 98/17238 | 4/1998 |

* cited by examiner

*Primary Examiner*—Sreeni Padmanabhan
*Assistant Examiner*—Gina C. Yu
(74) *Attorney, Agent, or Firm*—Greenblum & Bernstein, P.L.C.

(57) ABSTRACT

Water-in-oil emulsions comprising at least one cationic polymer, at least one surface active substance and a content of water and optional water-soluble substances totalling at least 80% based on the total weight of the emulsions.

8 Claims, No Drawings

PREPARATIONS OF THE W/O EMULSION TYPE WITH AN INCREASED WATER CONTENT, AND COMPRISING CATIONIC POLYMERS

Water-in-oil emulsions of high water content and comprising cationic polymers.

The present invention relates to cosmetic and dermatological preparations, in particular those comprised of water-in-oil emulsions, to processes for their preparation and to their use for cosmetic and medicinal purposes.

BACKGROUND OF THE INVENTION

The human skin is man's largest organ and performs a number of vital functions. Having an average area of about 2 $m^2$ in adults, human skin plays a prominent role as a protective and sensory organ. The purpose of this organ is to transmit and avert mechanical, thermal, actinic, chemical and biological stimuli. In addition, human skin plays an important role as a regulatory and target organ in human metabolism.

The main objective of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes), and also to assist the horny layer of the skin in its natural regeneration ability where damage has occurred.

If the barrier properties of the skin are impaired, increased resorption of toxic or allergenic substances or infection by microorganisms may result, leading to toxic or allergic skin reactions.

Another aim of skin care is to compensate for the loss by the skin of sebum and water caused by daily washing. This is particularly important if the natural regeneration ability of the skin is inadequate. Furthermore, skin care products should protect the skin against environmental influences, in particular against the effects of sun and wind, and delay skin ageing.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally understood to be heterogeneous systems which consist of two liquids which are immiscible with one another or which are miscible with one another only to a limited extent, and which are usually referred to as phases. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic structure being determined here by the oil.

The person skilled in the art is of course aware of a large number of ways to formulate stable W/O preparations for cosmetic or dermatological use, for example in the form of creams and ointments which can be spread in the temperature range of from room temperature to skin temperature, or as lotions and milks, which are more likely flowable in this temperature range. However, the prior art recognizes only a few formulations which are of such low viscosity that they would, for example, be sprayable.

In addition, low-viscosity preparations of the prior art often have the disadvantage that they are unstable and are limited to a narrow range of application or to a restricted choice of starting materials. Low-viscosity products in which, for example, strong polar oils—such as the vegetable oils frequently used in commercially available products— are sufficiently stabilized cannot therefore be currently found on the market.

W/O emulsions with a high water content and a low viscosity, which moreover have a storage stability which is required for marketable products can only be formulated according to the prior art in a very complex manner. Accordingly, the supply of such formulations is extremely low. Nevertheless, such formulations could offer the consumer cosmetic effects which are hitherto unknown.

The object of the present invention was to provide water-in-oil emulsion based preparations which have very low viscosity and which do not have the disadvantages of the prior art.

A further object of the present invention was to provide preparations which can be loaded with a high content of water-soluble and/or water-miscible substances having cosmetic or dermatological effectiveness, without impairing the galenical quality or other properties of the preparations.

According to K. J. Lissant: *The Geometry of High-Internal-Phase-Ratio Emulsions*; Journal of Colloid and Interface Science 22, 462–468 (1966), "high internal phase emulsions" are defined as emulsions with an internal phase of >70%.

In particular, the preparation of stable, flowable water-in-oil emulsions having a water content of more than 70% has proven to be very difficult. In particular, "high internal phase" W/O emulsions with a very high water content of more than 85% ("very high internal phase" W/O emulsions) are not accessible.

The preparation of stable, solid to flowable "high internal phase water-in-oil emulsions", in particular those with a water content higher than 80% by weight ("very high internal phase water-in-oil emulsions") and nevertheless with very good sensory properties is an unsolved problem. As a result of the very high water content in the emulsions, the latter "crack" on the skin particularly rapidly (sensorially unpleasant) into their main constituents (hydrophilic and lipophilic components). Furthermore, the lipophilic components also separate into their individual constituents, meaning that the lipids "slide away" from one another on the skin (sensorially unpleasant).

the technique of varying the phase/volume ratio (i.e. of incorporating higher amounts of liquid lipids), which is usually used for water-in-oil emulsions, can, because of the low lipid content, be used only to a limited extent in the case of "high internal phase" W/O emulsions, and not at all in the case of "very high internal phase" W/O emulsions. It is therefore only possible to obtain water-in-oil emulsions with a solid to semi-solid consistency. Even the use of polar lipids, which are usually used to obtain water-in-oil emulsions of lower viscosity, does not lead to the desired success.

SUMMARY OF THE INVENTION

Surprisingly, it has been found that water-in-oil emulsions
(a) with a content of water and optionally water-soluble substances totalling at least 80% by weight, and with a content of lipids, emulsifiers and lipophilic constituents of less than 20%, in each case based on the total weight of the preparations, (b) comprising at least one surface-active substance chosen from the group of substances of the general formula (I)

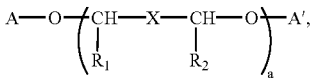

where A and A' are identical or different organic radicals chosen from the group consisting of branched and unbranched, saturated and unsaturated alkyl and acyl radicals and hydroxyacyl radicals having 10–30 carbon atoms, and also from the group of hydroxyacyl groups bonded together via ester functions, according to the scheme

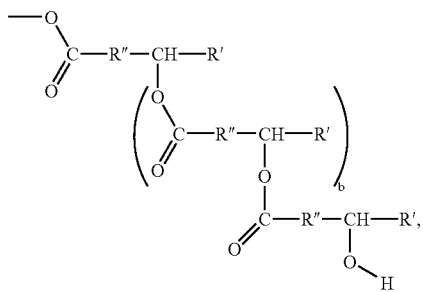

where R' is chosen from the group of branched and unbranched alkyl groups having 1 to 20 carbon atoms, and R'' is chosen from the group of branched and unbranched alkylene groups having 1 to 20 carbon atoms, and b is a number from 0 to 200, a is a number from 1 to 100, preferably from 2 to 60, in particular from 5 to 40, X is a single bond or the group

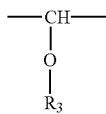

$R_1$ and $R_2$ independently of one another are chosen from the group consisting of H or methyl, $R_3$ is chosen from the group consisting of H, and of branched and unbranched, saturated and unsaturated alkyl- and acyl radicals having 1–20 carbon atoms, (c) additionally comprising at least one cationic polymer, overcome the disadvantages of the prior art.

DETAILED DESCRIPTION

The structural formula must not be interpreted as meaning that because of the index a, all of the radicals $R_1$, $R_2$ or $R_3$, represented in the brackets, are in each case identical throughout the entire molecule. Instead, these radicals can be chosen independently of each other in each of the a fragments

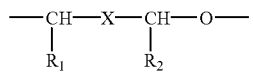

It is possible and advantageous to choose the total content of water and water-soluble substances in the W/O emulsions according to the invention to be greater than 80% by weight, in particular greater than 85% by weight, in each case based on the total weight of the preparations.

One example of surface-active substances which are to be used particularly advantageously for the purposes of the present invention is polyethylene glycol-30 dipolyhydroxystearate (PEG-30 dipolyhydroxystearate), which is sold by ICI Surfactants under the trade name ARLACEL® P135.

The total amount of surface-active substances used according to the invention in the finished cosmetic or dermatological preparations is advantageously chosen from the range 0.1–30% by weight, preferably 0.25–5.0% by weight, in particular 0.75–3.5% by weight, based on the total weight of the preparations.

Surprisingly, it has in particular been found that the addition of from 0.01 to 10% (preferably 0.25–1.25%) of suitable cationic polymers makes it possible to prepare stable, flowable "very high internal phase emulsions", which impart excellent sensory properties.

Suitable cationic polymers are, for example, cationic cellulose derivatives (e.g. Polymer JR 400® from Amerchol), cationic starch, copolymers of diallylammonium salts and acrylamides, quaternized vinylpyrrolidone/vinylimadazole polymers (e.g. Luviquat® from BASF), condensation products of polyglycols and amines, quaternized collagen polypeptides (e.g. Lamequat® L from Grünau-Henkel), quaternized wheat polypeptides, polyethyleneimine, cationic silicone polymers, copolymers of adipic acid with dimethylaminohydroxypropyldiethylenetriamine, copolymers of acrylic acid with dimethyldiallylammonium chloride (e.g. Merquat® 550 from Chemviron), polyaminopolyamides, cationic chitin derivatives, cationic guar gum (e.g. Jaguar® CBS from Hoechst Celanese), quaternized ammonium salt polymers (e.g. Mirapol® AD-1 from Miranol), and cationic biopolymers such as, for example, chitosan (average molecular weight from 50,000 to 2,000,000 g/mol [determined by means of gel permeation chromatography] and a degree of deacylation of from 10 to 99% [determined by means of $^1$H-NMR]).

Surprisingly, the preparations according to the invention are extremely pleasant to use on the skin and are characterized by very high cosmetic-elegance. Using the compositions, which are familiar to the person skilled in the art without further inventive activity, it is possible to achieve virtually any desired viscosities, from solid to flowable, meaning that the present invention can, for example, be formulated as a flowable application form (for example lotion) or as a semi-solid to solid preparation (for example as a cream).

For the purposes of the present disclosure, the general term for fats, oils, waxes and the like which is sometimes used is the term "lipids", which is entirely familiar to the person skilled in the art. The terms "oil phase" and "lipid phase" are also used synonymously.

In particular, it may be desired to impart a low viscosity to the preparations according to the invention, namely one which is lower than 5000 mPas [millipascal seconds]. For such cases, it is advantageous to formulate the oil phase such that it comprises at least 75% by weight of one or more substances chosen from the group consisting of nonpolar lipids which are liquid at room temperature which have a polarity greater than 30 mN/m, and/or silicone oils of any polarity where this proportion by weight is based on the total weight of the oil phase. Oils and fats differ from one another in their polarity, which is difficult to define. It has already being suggested to adopt the interfacial tension towards water as a measure of the polarity index of an oil or of an oil phase. By the method, the polarity of the oil phase in question is greater the lower the interfacial tension between this oil phase and water. According to the invention, the interfacial tension is regarded as one possible measure of the polarity of a given oil component.

The interfacial tension is the force which acts on an imaginary line one meter in length in the interface between two phases. The physical unit for this interfacial tension is conventionally calculated from the force/length relationship and is usually expressed in mN/m (millinewtons divided by meters). It has a positive sign if it endeavours to reduce the interface. In the converse case, it has a negative sign.

According to the invention, the limit below which an oil phase is "polar" and above which an oil phase is "non-polar" is regarded as 30 mN/m.

The following nonpolar lipids which are liquid at room temperature have proven particularly advantageous, hydrocarbons (mineral oils, cycloparaffin, polyisobutenes, polydecenes), non-ethoxylated or -propoxylated ethers (caprylyl ethers/Cetiol OE), and silicone oils (dimethicones, cylomethicones, dimethiconol).

According to the above definition of polarity, silicone oils are not considered nonpolar, but generally fall into the region of average polarity (typically between 20 and 30 mN/m).

If the intention is to obtain low-viscosity formulations, it is nevertheless possible to tolerate a certain content of polar lipids in the lipid mixture, it should then, however, usually not exceed 25% by weight, is preferably less than 15% by weight and should in the ideal case be no more than $\leq 10\%$ by weight, based on the total lipid phase.

According to the teaching presented here, in addition to higher viscosity formulations being obtainable, W/O emulsions can also be obtained whose viscosity at 25° C. is less than 5000 mPa.s (=millipascal seconds), in particular less than 4000 mPa.s, preferably less than 3500 mPa.s (HAAKE Viscotester VT-02).

In order to obtain preparations of higher viscosity, it is possible, in a simple manner, to lower the content of nonpolar oils (in accordance with the above definition) and increase the content of polar oils.

The oils according to the invention are advantageously likewise chosen from the group of paraffin oils, polyolefins, and Vaseline (petrolatum). Of the polyolefins, polydecenes and hydrogenated polyisobutene are the preferred substances.

For the purposes of the present invention, the oil phase can, provided the features listed in the claims are observed, additionally advantageously comprise substances chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms and from the group of esters of aromatic carboxylic acids and saturated and/or unsaturated, branched and/or unbranched alcohols having a chain length of from 3 to 30 carbon atoms.

Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, such as, for example, jojoba oil.

The oil phase can also be chosen advantageously from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24 carbon atoms, in particular 12–18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

If desired, fatty and/or wax components which are to be used advantageously in the oil phase can be chosen from the group of vegetable waxes, animal waxes, mineral waxes and petrochemical waxes. Examples which are favorable according to the invention are candelilla wax, carnauba wax, japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropigial grease, ceresin, ozocerite (earth wax), paraffin waxes and microcrystalline waxes.

Other advantageous fatty and/or wax components are chemically modified waxes and synthetic waxes such as, for example, those obtainable under the trade names Syncrowax HRC (glyceryl tribehenate), Syncrowax HGLC ($C_{16-36}$ fatty acid triglyceride) and Syncrowax AW 1C($C_{18-36}$ fatty acid) from CRODA GmbH, and also montane ester waxes, Sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkylstearate, $C_{20-40}$-alkylhydroxystearoyl stearate and/or glycol montanate. Also advantageous are certain organosilicon compounds, which have similar physical properties to the specified fatty and/or wax components, such as, for example, stearoxytrimethylsilane.

If desired, the fatty and/or wax components can be present either individually or as a mixture.

Any desired mixtures of such oil and wax components can also be used advantageously for the purposes of the present invention. In some instances, it can also be advantageous to use waxes, for example cetyl palmitate, as the lipid component of the oil phase.

Of the hydrocarbons, paraffin oil, hydrogenated polyolefins (e.g. hydrogenated polyisobutene), squalane and squalene can be used advantageously for the purposes of the present invention.

According to the invention, particularly advantageous emulsions are those which are characterized in that the oil phase consists of at least 50% by weight, preferably of more than 75% by weight, of at least one substance chosen from the group consisting of Vaseline (petrolatum), paraffin oil and polyolefins, preference being given amongst the latter to polydecenes.

The oil phase can advantageously additionally have a content of cyclic or linear silicone oils or consists entirely of such oils, although it is preferable to use an additional content of other oil phase components apart from the silicone oil or the silicone oils.

Cyclomethicones (e.g. cyclotetrasiloxane and cyclopentasiloxane) can be used advantageously. However, for the purposes of the present invention, it is also advantageous to use other silicone oils, for example dimethicones (polydimethyl-siloxanes of varying chain lengths such as, for example, Wacker AK 10, 20, 35, 50, 100) and polymethylphenylsiloxanes (such as, for example, phenyltrimethicones).

The aqueous phase of the preparations according to the invention optionally advantageously comprises alcohols, diols or polyols of low carbon number, and ethers thereof, preferably ethanol, isopropanol, propylene glycol, glycerol, ethylene glycol, ethylene glycol monoethyl ether of monobutyl ether, propylene glycol monomethyl, monoethyl or monobutyl ethers, diethylene glycol monomethyl or monoethyl ethers and analogous products, and also alcohols of low carbon number, e.g. ethanol, isopropanol, 1,2-propanediol, glycerol and, in particular, one or more thickeners which can advantageously be chosen from the group consisting of silicon dioxide, aluminium silicates, polysaccharides or derivatives thereof, e.g. hyaluronic acid, xanthan gum, hydroxypropylmethylcellulose, particularly advantageously from the group consisting of polyacrylates, preferably a polyacrylate from the group of Carbopols, for example Carbopol grades 980, 981, 1382, 2984, 5984, or also ETD (easy-to-disperse) grades 2001, 2020, 2050, in each case individually or in any combinations with one another.

A particular advantage of the present invention is that it permits high concentrations of polyols, in particular glycerol, to be used.

Particularly advantageous preparations are also obtained when antioxidants are used as additives or active ingredients. According to the invention, the preparations advantageously comprise one or more antioxidants. Antioxidants which are favorable but which are nevertheless optional may be all antioxidants which are customary or suitable for cosmetic and/or dermatological application.

The antioxidants are advantageously selected from the group consisting of amino acids (e.g. glycine, histidine, tyrosine, tryptophan) and their derivatives, imidazoles, (e.g. urocanic acid) and their derivatives, peptides, such as D,L-camosine, D-camosine, L-camosin and their derivatives (.g. anserine), carotenoids, carotenes (e.g. α-carotene, γ-carotene, ψ-lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, hepta-thionine sulphoximine) in very low tolerated doses (e.g. pmol to µmol/kg), and also (metal) chelating agents (e.g. α-hydroxy fatty acids, palmitic acid, phytic add, lactoferrin), α-hydroxy acids (e.g. citric add, lactic acid, malic acid), humic acid, bile acid, bile extracts, bilirubin, biliverdin, EDTA, EGTA and their derivatives, unsaturated fatty adds and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and its derivatives, ferulic add and its derivatives, butylated hydroxytoluene, butylated hydroxyanisole, nordihydroguaiac acid, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active ingredients which are suitable according to the invention.

For the purposes of the present invention, oil-soluble antioxidants can be used particularly advantageously.

A surprising property of the present invention is that preparations according to the inventions are very good vehicles for cosmetic or dermatological active ingredients into the skin, preferred active ingredients being antioxidants which are able to protect the skin against oxidative stress. Preferred antioxidants are Vitamin E and its derivatives and Vitamin A and its derivatives.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or its derivatives are used as the antioxidant or antioxidants, their respective concentrations are advantageously chosen from the range of 0.001–10% by weight, based on the total weight of the formulation.

If vitamin A or vitamin A derivatives or carotenes or their derivatives are used as the antioxidant or antioxidants, their respective concentrations are advantageously chosen from the range of 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a colouring action, thickeners, surface-active substances, emulsifiers, emollients, moisturizers and/or humectants, anti-inflammatory substances, additional active ingredients such as vitamins or proteins, sunscreens, insect repellants, bacteriocides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulphates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only a physiologically acceptable electrolyte should be used in cosmetics. Particular preference is given to potassium chloride, sodium chloride, magnesium sulphate, zinc sulphate and mixtures thereof.

Corresponding requirements apply mutatis mutandis to the formulation of medicinal preparations.

The W/O emulsions according to the invention can be used as bases for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in admixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorinated hydrocarbons and chlorofluorocarbons (CFCs).

Cosmetic and dermatological preparations which are in the form of a sunscreen are also favourable. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can advantageously comprise further substances which absorb UV radiation in the UV-B region, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for hair and skin.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;
4-aminobenzoic add derivatives, preferably 2-ethylhexyl 4-(dimethyl-amino)benzoate, amyl 4-(dimethylamino) benzoate;
esters of cinnamic acid, preferably 2-ethylhexyl 4-methoxycinnamate, isopentyl 4-methoxycinnamate;
esters of salicylic add, preferably 2-ethylhexyl salicylate, 4-isopropylbenzyl salicylate, homomenthyl salicylate;
derivatives of benzophenone, preferably 2-hydroxy-4-methoxybenzophenone, 2-hydroxy-4-methoxy-4'-methylbenzophenone, 2,2'-dihydroxy-4-methoxybenzophenone;
esters of benzalmalonic add, preferably di(2-ethylhexyl) 4-methoxybenzalmalonate;
derivatives of 1,3,5-triazine, preferably 2,4,6-trianilino(p-carbo-2'-ethyl-1'-hexyloxy) 1,3,5-triazine.

The list of said UV-B filters, which may be used in combination with the novel active ingredient combinations, is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide.

Further constituents which can be used are:
fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
alcohols, diols or polyols of low carbon number, and their ethers, preferably ethanol, isopropanol, propylene glycol, glycerol, ethylene glycol, ethylene glycol-monoethyl or monobutyl ethers, propylene glycol monomethyl, monoethyl or monobutyl ethers, diethylene glycol monomethyl or monoethyl ethers and analogous products.

Preparations according to the invention can also comprise active ingredients (one or more compounds) which are chosen from the group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favourably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of a vegetable and animal origin, e.g. evening primrose oil, star flower oil or currant seed oil, fish oils, cod-liver oil or also ceramides or ceramide-like compounds etc. It is also advantageous to choose the active ingredients from the group of refatting substances, for example purcellin oil, EuceritÓ and NeoceritÓ.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

The examples below serve to illustrate the present invention without limiting it. The numerical values in the examples refer to percentages by weight, based on the total weight of the respective preparations.

EXAMPLE 1 (W/O CR AM)

|  | % by weight |
| --- | --- |
| PEG-30 Dipolyhydroxystearate | 1.50 |
| Caprylic acid/capric acid triglycerides | 4.00 |
| Dicaprylyl ether | 3.00 |
| Octyldodecanol | 3.00 |
| Glycerol | 3.00 |
| Sodium chloride | 0.70 |
| Chitosan | 1.00 |
| Lactic acid | 0.90 |
| Perfume, preservative, dyes, antioxidants | q.s. |
| Water | ad 100.0 0 |

EXAMPLE 2 (W/O LOTION)

|  | % by weight |
| --- | --- |
| PEG-30 Dipolyhydroxystearate | 2.00 |
| Isohexadecane | 4.50 |
| Paraffinum liquidum | 4.50 |
| Glycerol | 3.00 |
| Magnesium sulphate | 0.70 |
| Polyquaternium-10 | 1.00 |
| Perfume, preservative, dyes, antioxidants | q.s. |
| Water | ad 100.00 |

EXAMPLE 3 (W/O LOTION)

|  | % by weight |
| --- | --- |
| PEG-30 Dipolyhydroxystearate | 2.00 |
| Squalane | 3.00 |
| Paraffinum liquidum | 3.00 |
| Hydrogenated polysiobutene | 3.00 |
| Glycerol | 3.00 |
| Sodium chloride | 0.70 |
| Chitosan | 0.75 |
| Lactic acid | 0.60 |
| Perfume, preservative, dyes, antioxidants | q.s. |
| Water | ad 100.00 |

EXAMPLE 4 (W/O CR AM)

|  | % by weight |
| --- | --- |
| PEG-30 Dipolyhydroxystearate | 2.00 |
| Paraffinum liquidum | 9.00 |
| Tocopherol acetate | 0.50 |
| Glycerol | 3.00 |
| Panthenol | 0.30 |
| 1,3-Butyleneglycol | 1.00 |
| Serine | 0.30 |
| Biotin | 0.10 |
| Distarch phosphate | 1.00 |
| Magnesium sulphate | 0.70 |
| Polyquaternium-10 | 0.25 |
| Perfume, preservative, dyes, antioxidants | q.s. |
| Water | ad 100.00 |

EXAMPLE 5 (W/O CR AM)

|  | % by weight |
| --- | --- |
| PEG-30 Dipolyhydroxystearate | 2.00 |
| Isohexadecane | 2.00 |
| Paraffinum liquidum | 2.00 |
| Butylmethoxydibenzoylmethane | 1.00 |
| Octyl methoxycinnamate | 2.00 |
| Methylbenzylidenecamphor | 2.00 |
| Octyltriazone | 0.50 |
| Titanium dioxide | 1.00 |
| Zinc oxide | 1.00 |
| Glycerol | 1.00 |
| Magnesium sulphate | 0.70 |
| Polyquaternium-10 | 0.25 |
| Perfume, preservative, dyes, antioxidants | q.s. |
| Water | ad 100.00 |

EXAMPLE 6 (W/O LOTION)

|  | % by weight |
| --- | --- |
| PEG-30 Dipolyhydroxystearate | 2.00 |
| Isohexadecane | 4.50 |
| Paraffinum subliquidum | 4.50 |
| Glycerol | 3.00 |
| Sodium chloride | 0.70 |
| Chitosan | 2.50 |
| Lactic acid | 1.80 |
| Perfume, preservative, dyes, antioxidants | q.s. |
| Water | ad 100.00 |

EXAMPLE 7 (W/O CR AM)

|  | % by weight |
| --- | --- |
| PEG-30 Dipolyhydroxystearate | 2.00 |
| Caprylic acidlcapric acid triglycerides | 4.00 |
| Dicaprylyl ether | 2.50 |
| Octyldodecanol | 2.50 |
| Glycerol | 20.00 |
| Propylene glycol | 15.00 |
| Sodium chloride | 0.70 |
| Chitosan | 1.00 |
| Lactic acid | 0.60 |
| Perfume, preservative, dyes, antioxidants | q.s. |
| Water | ad 100.00 |

EXAMPLE 8 (EMULSION MAKE-UP)

|  | % by weight |
|---|---|
| PEG-30 Dipolyhydroxystearate | 2.00 |
| Octyldodecanol | 2.00 |
| $C_{12-15}$ alkyl benzoates | 2.00 |
| Squalane | 1.00 |
| Paraffinum liquidum | 1.00 |
| Distarch phosphate | 0.50 |
| Dimethicone | 0.50 |
| Glycerol | 1.50 |
| Magnesium silicate | 1.00 |
| Sodium chloride | 0.70 |
| Chitosan | 1.00 |
| Lactic acid | 0.60 |
| Mica | 0.50 |
| Iron oxides | 0.50 |
| Titanium dioxide | 1.00 |
| Talc | 1.00 |
| Tapioca starch | 0.25 |
| Perfume, preservative, dyes, antioxidants | q.s. |
| Water | ad 100.00 |

What is claimed is:

1. A water-in-oil emulsion
(a) with a content of water and optionally water-soluble substances totalling greater than 85% by weight, and with a content of lipids, emulsifiers and lipophilic constituents of less than 15% by weight, in each case based on the total weight of the preparations,
(b) comprising at least one surface-active substance selected from the group consisting of substances of the general formula (I)

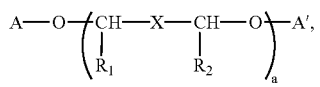

where A and A' are identical or different organic radicals selected from the group consisting of branched and unbranched, saturated and unsaturated alkyl and acyl radicals and hydroxyacyl radicals having 10–30 carbon atoms, and the group consisting of hydroxyacyl groups bonded together via ester functions, according to the scheme

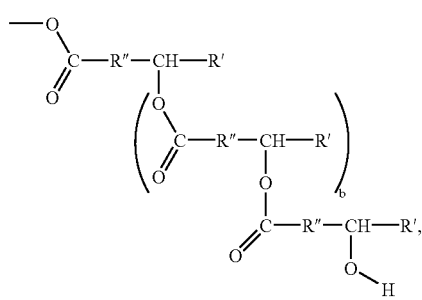

where R' is selected from the group consisting of branched and unbranched alkyl groups having 1 to 20 carbon atoms, and R" is selected from the group consisting of branched and unbranched alkylene groups having 1 to 20 carbon atoms, and b is a number from 0 to 200, a is a number from 1 to 100, X is a single bond or the group

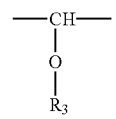

$R_1$ and $R_2$ independently of one another are selected from the group consisting of H and methyl, $R_3$ is selected from the group consisting of H, and of branched and unbranched, saturated and unsaturated alkyl- and acyl radicals having 1–20 carbon atoms, (c) additionally comprising at least one cationic polymer, wherein said at least one cationic polymer is selected from the group consisting of cationic cellulose derivatized with a quaternary ammonium salt, cationic starch, copolymers of diallylammonium salts and acrylamides, quaternized vinylpyrrolidone/vinylimadazole polymers, condensation products of a polyglycol with an amine, quaternized collagen polypeptides, quaternized wheat polypeptides, polyethyleneimine, cationic silicone polymers, copolymers of adipic acid with dimethylaminohydroxypropyldiethylenetriamine, copolymers of acrylic acid with dimethyldiallylammonium chloride, polyaminopolyamides, and cationic guar gum.

2. Emulsion according to claim 1, wherein the surface-active substance is polyethylene glycol-30 dihydroxystearate.

3. Emulsion according to claim 1, wherein the oil phase comprises at least 50% by weight of at least one substance selected from the group consisting of petrolatum, paraffin oil and polyolefins.

4. Emulsion according to claim 1, comprising from 0.01 to 10% by weight of cationic polymers.

5. Emulsion according to claim 1, wherein a is a number from 2 to 60.

6. Emulsion according to claim 5, wherein a is a number from 5 to 40.

7. Emulsion according to claim 4, wherein said amount of cationic polymers is from 0.25 to 1.25% by weight.

8. The emulsion according to claim 1 wherein the cationic cellulose derivatized with quaternium ammonium salt is polyquaternium-10.

* * * * *

UNITED STATES PATENT AND TRADEMARK OFFICE
CERTIFICATE OF CORRECTION

PATENT NO.         : 7,138,128 B2  
APPLICATION NO. : 09/436171  
DATED              : November 21, 2006  
INVENTOR(S)       : Andreas Bleckmann It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (561) days Delete the phrase "by 561 days" and insert -- by 610 days--

Signed and Sealed this

Eighteenth Day of December, 2007

JON W. DUDAS  
*Director of the United States Patent and Trademark Office*